US00PP24538P2

(12) United States Plant Patent
Green, Jr.

(10) Patent No.: US PP24,538 P2
(45) Date of Patent: Jun. 10, 2014

(54) ***CAMELLIA* PLANT NAMED 'GREEN 02-003'**

(50) Latin Name: *Camellia sasanqua*
Varietal Denomination: Green 02-003

(71) Applicant: Robert M. Green, Jr., Fairhope, AL (US)

(72) Inventor: Robert M. Green, Jr., Fairhope, AL (US)

(73) Assignee: Plants Nouveau, LLC, Charleston, SC (US)

( * ) Notice: Subject to any disclaimer, the term of this patent is extended or adjusted under 35 U.S.C. 154(b) by 3 days.

(21) Appl. No.: 13/694,875

(22) Filed: Jan. 14, 2013

(51) Int. Cl.
*A01H 5/00* (2006.01)

(52) U.S. Cl.
USPC ..... Plt./245

(58) Field of Classification Search
USPC ..... Plt./245
See application file for complete search history.

*Primary Examiner* — Anne Grunberg
(74) *Attorney, Agent, or Firm* — Penny J. Aguirre

(57) ABSTRACT

A new cultivar of *Camellia sasanqua* named 'Green 02-003', characterized by its very compact and spreading to rounded plant habit, its profuse blooming habit and blooms at a young age, its double flowers (peony-form) that are red in color, its very glossy foliage, its good resistance to *Phytophora* sp. and *Glomerella*, and its ability to be readily propagated by stem cuttings.

2 Drawing Sheets

Botanical classification: *Camellia sasanqua.*
Variety denomination: 'Green 02-003'.

BACKGROUND OF THE INVENTION

The present invention relates to a new and distinct cultivar of *Camellia sasanqua*. The new cultivar will be referred to hereafter by its cultivar name, 'Green 02-003'. 'Green 02-003' is grown for use as a landscape shrub.

The new *Camellia* arose from on ongoing breeding program conducted by the Inventor in Fairhope, Ala. that began in 1992. The objective of the breeding program is to produce new cultivars of *Camellia* with compact plant habits, vigorous growth habits, and extended bloom periods. 'Green 02-003' originated as a whole plant mutation that arose from seed planted from open pollination of unnamed plants of *Camellia* from the Inventor's breeding line in fall of 2002. The specific parents are therefore unknown. The new *Camellia* was selected as a single unique plant in fall of 2005 after evaluation of 1400 seedlings.

The new cultivar was first asexually propagated by stem cutting by the Inventor in summer of 2006 in Fairhope, Ala. Asexual propagation by stem cuttings has determined that the characteristics of this cultivar are stable and are reproduced true to type in successive generations.

SUMMARY OF THE INVENTION

The following traits have been repeatedly observed and represent the characteristics of the new *Camellia* as observed in Fairhope, Ala. These attributes in combination distinguish 'Green 02-003' as a unique cultivar of *Camellia.*

1. 'Green 02-003' exhibits a very compact, spreading to rounded plant habit.
2. 'Green 02-003' exhibits a profuse blooming habit and blooms at a young age (observed on plants 24 months in age).
3. 'Green 02-003' exhibits double flowers (peony-form) that are red in color.

4. 'Green 02-003' exhibits very glossy foliage.
5. 'Green 02-003' has shown good resistance to *Phytophora* sp. and *Glomerella.*
6. 'Green 02-003' is readily propagated by stem cuttings.

The new cultivar of *Camellia* can be readily distinguished from other cultivars. 'Green 02-003' can most closely compared to the cultivars 'Yuletide' (not patented) and 'Green 94-035' (U.S. Plant Pat. No. 20,465). 'Yuletide' is similar to 'Green 02-003' in having red flowers. 'Yuletide' differs from 'Green 02-003' in having single flowers, in having a less compact plant habit, and exhibiting a decrease in bloom on older plants in the landscape. 'Green 94-035' is similar to 'Green 02-003' in having a compact plant habit, in being floriferous, and in having similar foliage size. 'Green 94-035' differs from 'Green 02-003' in being having a less spreading plant habit and in having flowers that are muti-hued pink.

BRIEF DESCRIPTION OF THE DRAWING

The accompanying colored photographs illustrate the overall appearance and distinct characteristics of the new *Camellia*, 'Green 02-003', as grown in Fairhope, Ala. The photographs were taken of four year-old plants of 'Green 02-003' as grown in a trial garden in in Fairhope, Ala.

DETAILED BOTANICAL DESCRIPTION

Figure 1:
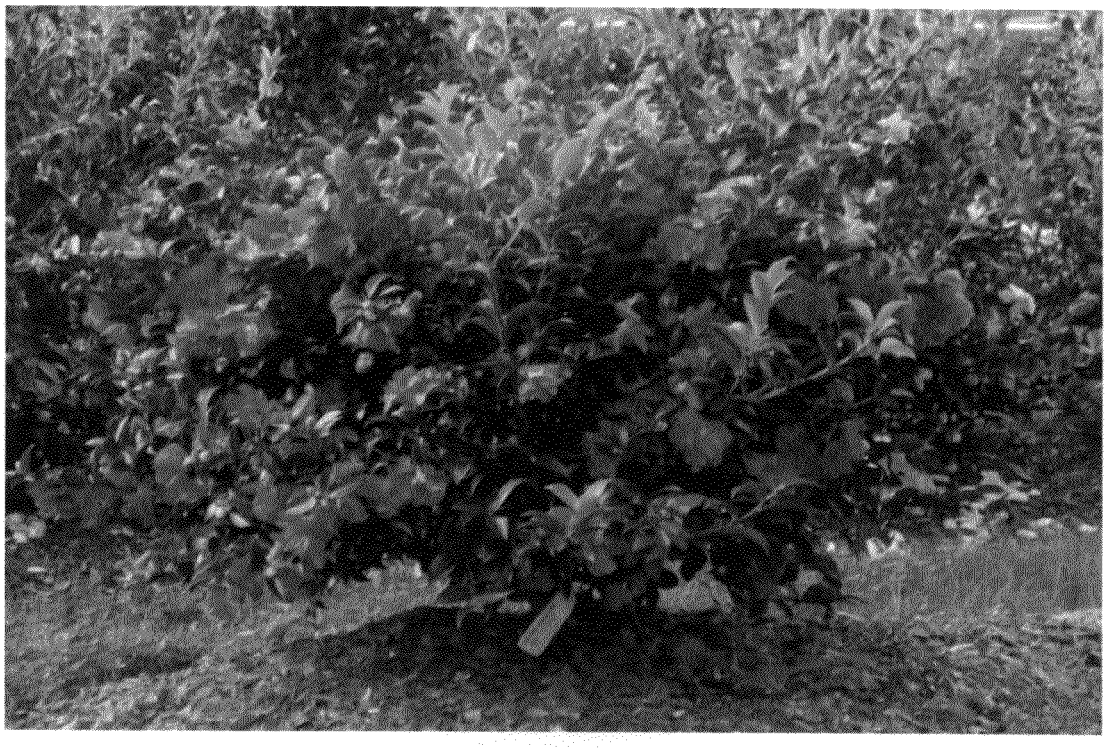
FIG. 1 provides view of the plant habit and profuse blooming of 'Green 02-003'.
Figure 2:
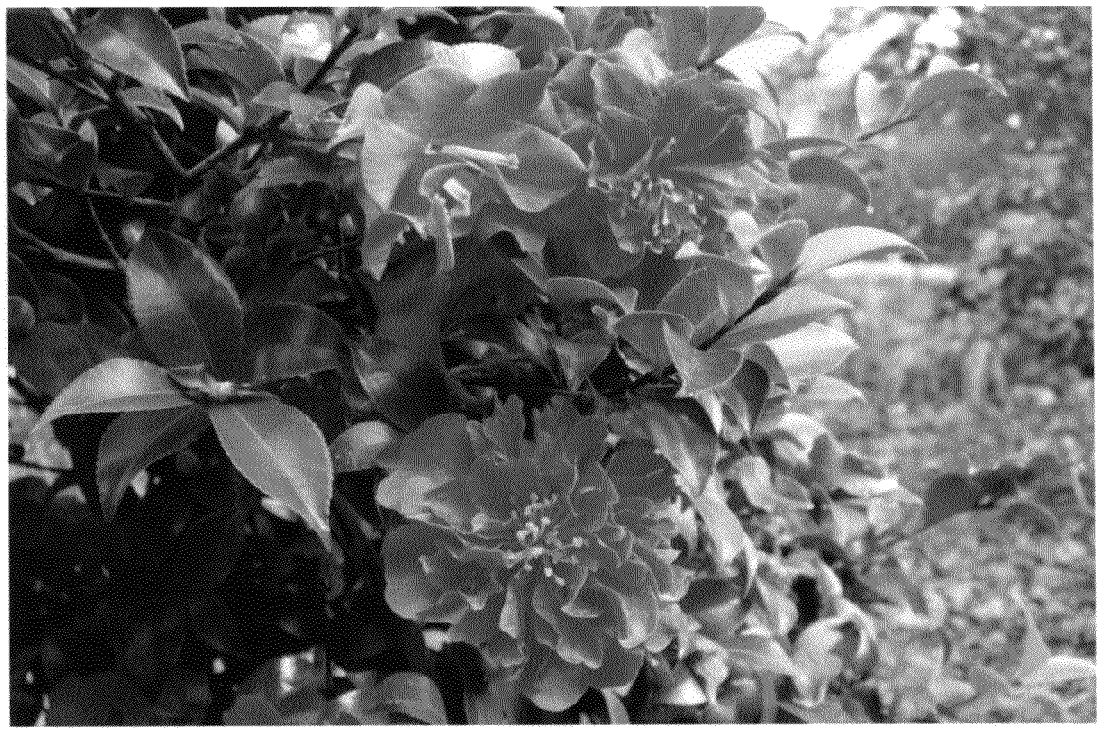
FIG. 2 provides a close-up view of flowers of 'Green 02-003'. The colors in the photographs are as close as possible with digital photography techniques available, the color values cited in the detailed botanical description accurately describe the colors of the new *Camellia.*

The following is a detailed description of the new cultivar as observed on 36 month-old plants of 'Green 02-003' as grown outdoors under 30% shade cloth in 3-gallon containers in Fairhope, Ala. Plants were grown under average day temperatures of 50 to 75° F. and average night temperatures of 30 to 50° F. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming habit*.—Seven to eight weeks in mid-fall to late fall in Fairhope, Ala.

*Plant type*.—Evergreen shrub.

*Plant habit*.—Very compact, spreading to rounded form.

*Height and spread*.—Up to 5 feet in height and width.

*Cold hardiness*.—At least in U.S.D.A. Zones 7a to 9.

*Diseases and pests*.—Has shown resistance to *Phytophora* sp. and *Glomerella*.

*Propagation*.—Stem cuttings.

*Growth rate*.—Moderate.

*Roots*.—Fibrous.

Branch description:

*Stem shape*.—Round.

*Stem strength*.—Strong.

*Stem color*.—Young; 166A, mature bark; 199C flushed with N199C.

*Stem size*.—Lateral branches; range from 30.5 to 35.5 cm in length and 4 mm in width.

*Stem surface*.—Young; glabrous and smooth, adult wood; bark-like, slightly rough to touch.

*Branching*.—Densely branched with an average of 30 lateral branches.

*Internode length*.—Range from 2.5 to 7.6 cm.

Foliage description:

*Leaf shape*.—Elliptic to slightly ovate.

*Leaf division*.—Simple.

*Leaf base*.—Attenuate.

*Leaf apex*.—Acuminate.

*Leaf fragrance*.—None.

*Leaf venation*.—Pinnate, midrib upper surface center 145A in color, mid rib lower surface center N144A, other viens match leaf color.

*Leaf margins*.—Serrate.

*Leaf arrangement*.—Alternate.

*Leaf attachment*.—Petiolate.

*Leaf substance*.—Thick and leathery with a high tolerance to stress.

*Leaf surface*.—Smooth, highly glossy on upper surface, glossy and smooth on lower surface.

*Leaf size*.—Average of 4.5 cm in length and 1 cm in width.

*Leaf color*.—Young and mature leaves upper surface; a blend of 139A and N137A, young and mature leaves lower surface; 146A.

*Petioles*.—Flattened with a width of 1 mm and a length of 3 mm and upper and lower surface is 144A in color.

*Stipules*.—None.

Inflorescence description:

*Inflorescence type*.—Solitary at upper nodes.

*Flower number*.—6 to 8 per lateral stem.

*Flower fragrance*.—Slightly fragrant.

*Flower longevity*.—About one week, self cleaning.

*Flower type*.—Fully double, peony form.

*Flower aspect*.—Outward and upward.

*Flower size*.—Average of 5.5 cm in diameter and 3.5 cm in depth.

*Peduncles*.—About 1 mm in length and diameter, 144B in color, glabrous suface.

*Flower buds*.—Ovate in shape, average of 2 cm in length and 1.5 width, color; bract pertion 147B, sepal portion a blend of 144B and 146B with margins of sepals 60A and apex 60A.

*Sepals*.—About 6, ovate in shape and strongly cupped inward, imbricate, margin is entire, color of upper and lower surface; a blend of 146A and 147B with apex 60A to 60B, both surfaces are glabrous and shiny, average of 1.2 cm in length and 8 mm in width, apex is obtuse, base is truncate/rounded.

*Petals*.—24 to 27, cordate or orbicular in shape, upper and lower surface is glabrous and dull, margin entire and occasionaly with slight undulations, apex cordate to rounded, broadly cuneate base, average of 2.5 cm in length and width, color: opening and fully open flowers upper and lower surface; a blend of 60A, 60B, and 60C with some suffusion of 59A toward apex.

*Petaloids*.—3 to 5, cordate to irregular in shape, upper and lower surface glabrous and dull, entire margin but slightly wavy with apex typically cordate, average of 1.8 cm in length and 1.4 mm in width, color upper and lower surface when opening and fully open; a blend of 60A, 60B, and 60C with some suffusion of 59A toward apex.

Reproductive organs:

*Pistil*.—1, compound, 3 to 5 styles are about 1 cm in length and 0.7 mm in width and 145C in color, stigmas are very minute at tips of styles and 145B in color, ovary is superior, ovate in shape, 3 mm in diameter and 2 mm in depth, 145B in color and covered with hairs.

*Stamens*.—12 to 14, filaments are about 1 cm in length, 0.7 mm in width and 158D in color, anthers are oblong-wedge shaped, dorsifixed, an average of 2 mm in length and 1 mm in width and 145D in color, pollen abundant and 11A in color.

*Fruit/seeds*.—Have not been observed.

It is claimed:

1. a new and distinct cultivar of *Camellia* plant named 'Green 02-003' as herein illustrated and described.

* * * * *